(12) United States Patent
Allemann et al.

(10) Patent No.: US 7,387,563 B2
(45) Date of Patent: Jun. 17, 2008

(54) MANDREL AND ACCESSORY AND RELATED COMBINATION FOR USE WITH A ROTARY TOOL

(75) Inventors: Markus Allemann, Grayslake, IL (US); Edward G. Ennis, Niles, IL (US); Vera Maras, Schaumburg, IL (US); Jose Nieto, Chicago, IL (US); Bradley J. Albrecht, Cahokia, IL (US); Simon C. Dirnberger, Tulsa, OK (US); Alan S. Kremzar, Cedar Rapids, IA (US); Michael C. Mayer, Smithshire, IL (US); Alexandria L. Merritt, Hannibal, MO (US); Amanda B. Raffurty, Lee's Summit, MO (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/187,139

(22) Filed: Jul. 21, 2005

(65) Prior Publication Data
US 2007/0021044 A1    Jan. 25, 2007

(51) Int. Cl.
*B24B 23/02* (2006.01)
(52) U.S. Cl. ........................... 451/342; 451/508
(58) Field of Classification Search ................. 451/342, 451/911, 509, 514
See application file for complete search history.

(56) References Cited

U.S. PATENT DOCUMENTS

| | | | |
|---|---|---|---|
| 480,121 A | 8/1892 | Nichols | |
| 505,121 A | 9/1893 | Nelson | |
| 514,882 A | 2/1894 | Elliott | |
| 583,472 A | 6/1897 | Heath, Jr. | |
| 769,426 A | 9/1904 | Zeran | |
| 1,130,716 A * | 3/1915 | Dressel | 433/134 |
| 1,333,054 A | 3/1920 | Abbott | |
| 1,941,840 A | 1/1934 | Kelsey | |
| 1,947,662 A * | 2/1934 | Robinson | 451/342 |
| 1,987,830 A * | 1/1935 | Kelsey | 433/134 |
| 2,030,910 A * | 2/1936 | Blair | 433/135 |
| 2,276,067 A | 3/1942 | Siqveland | |
| 4,527,360 A | 7/1985 | Dicke | |
| 4,561,217 A * | 12/1985 | Steyskal | 451/342 |
| 4,730,952 A * | 3/1988 | Wiley | 403/316 |
| 4,889,489 A | 12/1989 | Von Weissenfluh | |
| 5,303,688 A * | 4/1994 | Chiuminatta et al. | 125/15 |

FOREIGN PATENT DOCUMENTS

EP        0 832 614        4/1998
WO        WO 98/43779      10/1998

* cited by examiner

*Primary Examiner*—Robert Rose
(74) *Attorney, Agent, or Firm*—Maginot, Moore & Beck (57) ABSTRACT

A mandrel and accessory and related combination for use with a rotary tool are disclosed. For instance, the mandrel and accessory combination includes a mandrel assembly and an accessory. The mandrel assembly includes (i) a shaft component defining an axis and having a first portion configured to be received in a chuck of a power tool, and a second portion having a first shaft tooth and a second shaft tooth each extending in a perpendicular manner with respect to the axis, and (ii) a collar component defining a passage through which the shaft component extends, the collar component having a first collar tooth and a second collar tooth. The accessory includes an outer wall structure defining a circular outer periphery; and an inner wall structure defining a coupling opening. The accessory is configured to be releasably coupled to the mandrel assembly.

39 Claims, 11 Drawing Sheets

MANDREL AND ACCESSORY AND RELATED COMBINATION FOR USE WITH A ROTARY TOOL

BACKGROUND

This invention relates to the field of hand held rotary tools and related accessories.

Hand held rotary tools are widely used by many people, including craftspeople, homeowners, and artists. These rotary tools typically include an outer housing designed to be easily held within a human hand. The housing retains an electric motor which is operable to drive a rotatable chuck of the rotary tool. A mandrel may be releasably coupled to the chuck so as to be rotatably driven by the rotary tool. In turn, an accessory may be releasably secured to the mandrel thereby enabling the rotary tool to rotatably drive the accessory. The accessory may be a cut-off wheel, a polishing wheel, a grinding wheel, a sanding disc, or any other similar member.

There exists a variety of mandrels that are configured to releasably secure an accessory thereto. One such mandrel includes a base having a threaded aperture and a clamping screw that cooperate to clamp the accessory to the mandrel between the base and the clamping screw. With the accessory so clamped, rotation of the mandrel by the rotary tool causes rotation of the accessory thereby allowing the user to perform work on a workpiece.

In order to change an accessory that is secured to a mandrel of the type described above, it is typically necessary to loosen the clamping screw from the base. Of course, in order to loosen the clamping screw, the user must first obtain an appropriately sized screwdriver, which may not be immediately available to the user. Furthermore, some users find the task of turning a screw tedious. Also, once the clamping screw is separated from meshing engagement from the base, the clamping screw is susceptible to being inadvertently dropped and lost since it is a relatively small, separate component. Accordingly, it would be advantageous to provide a mandrel and associated accessory that is quick and easy to use and does not require the use of an additional tool such as a screwdriver, or the use of a relatively small, separate component such as a clamping screw.

SUMMARY

In accordance with one embodiment of the present invention, there is provided a mandrel and accessory combination that includes a mandrel assembly and an accessory. The mandrel assembly includes a shaft component defining an axis and having (i) a first portion configured to be received in a chuck of a power tool, and (ii) a second portion having a first shaft tooth and a second shaft tooth each extending in a perpendicular manner with respect to the axis; and a collar component defining a passage through which the shaft component extends, the collar component having a first collar tooth and a second collar tooth. The accessory includes an outer wall structure defining a circular outer periphery; and an inner wall structure defining a coupling opening. The inner wall structure includes (i) a first inner wall portion defining a first arc of a first circle having a first diameter, (ii) a second inner wall portion defining a second arc of the first circle having the first diameter, (iii) a third inner wall portion defining a third arc of a second circle having a second diameter, and (iv) a fourth inner wall portion defining a fourth arc of the second circle having the second diameter. The first shaft tooth includes a first outer shaft tooth wall portion defining a fifth arc of a third circle having a third diameter. The second shaft tooth includes a second outer shaft tooth wall portion defining a sixth arc of the third circle having the third diameter. The first collar tooth includes a first outer collar tooth wall portion defining a seventh arc of the third circle having the third diameter. The second collar tooth includes a second outer collar tooth wall portion defining an eighth arc of the third circle having the third diameter. The first diameter is greater than the second diameter, the first diameter is greater than the third diameter, and second diameter is less than the third diameter.

In accordance with another embodiment of the present invention there is provided a mandrel assembly having a shaft component and a collar component. The shaft component defines an axis and has (i) a first portion configured to be received in a chuck of a power tool, and (ii) a second portion having a first shaft tooth and a second shaft tooth each extending in a perpendicular manner with respect to the axis. The collar component defines a passage through which the shaft component extends, the collar component having a first collar tooth and a second collar tooth. The first shaft tooth includes a first outer shaft tooth wall portion defining a first arc of a circle having a diameter. The second shaft tooth includes a second outer shaft tooth wall portion defining a second arc of the circle having the diameter. The first collar tooth includes a first outer collar tooth wall portion defining a third arc of the circle having the diameter. And the second collar tooth includes a second outer collar tooth wall portion defining a fourth arc of the circle having the diameter.

Pursuant to yet another embodiment, there is provided a rotary tool accessory that includes an outer wall structure defining a circular outer periphery, and an inner wall structure defining a coupling opening. The inner wall structure includes (i) a first inner wall portion, (ii) second inner wall portion, (iii) a third inner wall portion, and (iv) a fourth inner wall portion. The first inner wall portion defines a first arc of a first circle having a first diameter. The second inner wall portion defines a second arc of the first circle having the first diameter. The third inner wall portion defines a third arc of a second circle having a second diameter. The fourth inner wall portion defines a fourth arc of the second circle having the second diameter. In addition, first diameter is greater than the second diameter.

In accordance with still another embodiment, there is provided a rotary tool accessory that includes a workpiece contacting portion, and an inner wall structure defining a coupling opening. The inner wall structure includes (i) a first inner wall portion, and (ii) second inner wall portion. The first inner wall portion defines a first arc of a first circle having a first diameter. The second inner wall portion defines a second arc of a second circle having a second diameter. Moreover, the first diameter is greater than the second diameter.

DESCRIPTION

Figure 1:
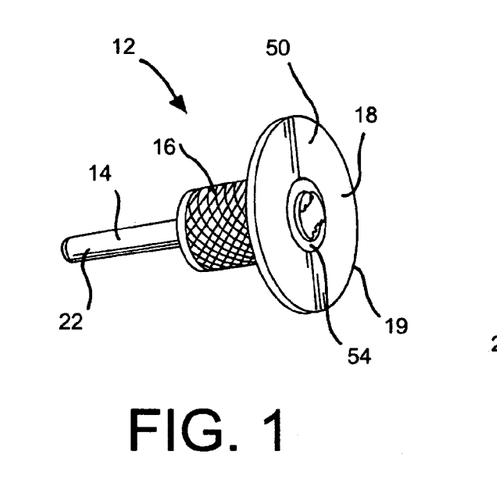
FIG. 1 shows a front perspective view of a mandrel assembly for use with a rotary tool having an accessory attached thereto.
Figure 2:
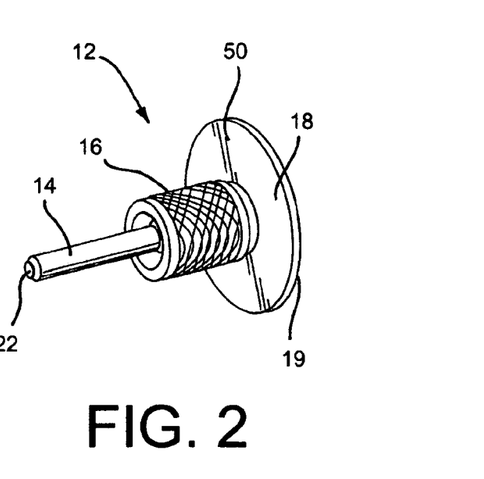
FIG. 2 shows a rear perspective view of the mandrel assembly and accessory of FIG. 1.
Figure 3:
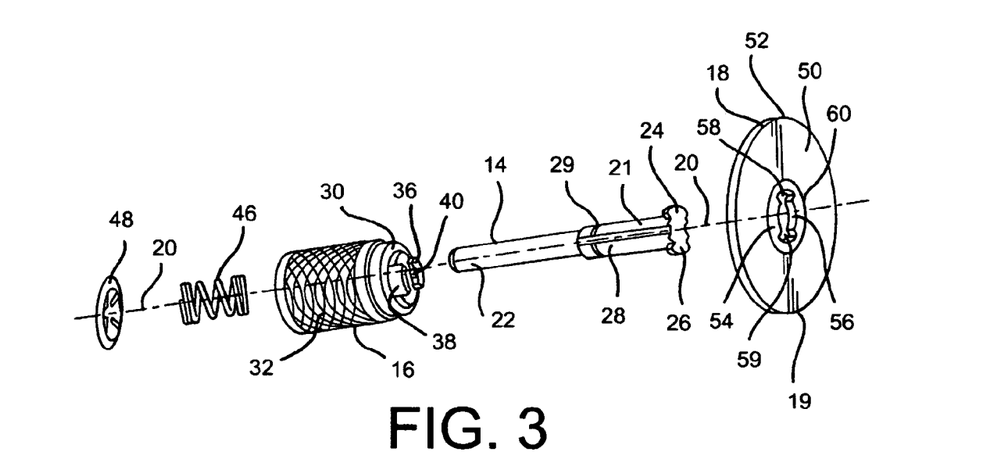
FIG. 3 shows an exploded perspective view of the mandrel assembly and accessory of FIG. 1.

A mandrel assembly for use with a rotary tool is shown in FIGS. 1–3. The mandrel assembly 12 includes a mandrel shaft 14 and a collar 16 slideable along the mandrel shaft. An accessory 18 in the form of a cut-off wheel 19 is configured to be releasably attached to the mandrel assembly. The mandrel shaft 14 of the mandrel assembly 12 is designed to be releasably coupled to a chuck of a rotary tool which includes an electric motor (not shown). Operation of the rotary tool rotates the chuck which in turn rotates the mandrel shaft 14 thereby imparting rotary movement to the cut-off wheel 19.

Figure 7:
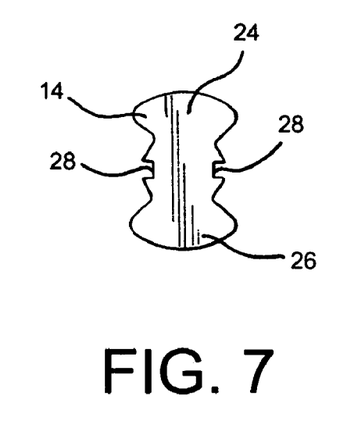
FIG. 7 shows a top elevational view of a shaft of the mandrel assembly of FIG. 5.
Figure 8:
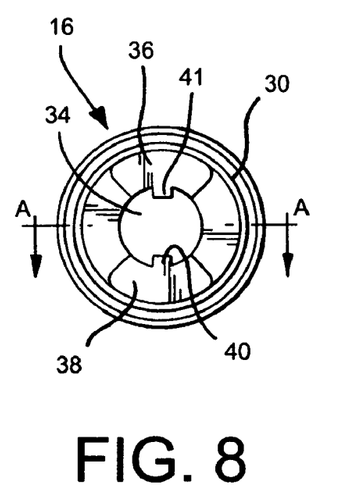
FIG. 8 shows a front elevational view of a collar of the mandrel assembly of FIG. 5.

The mandrel shaft 14 is comprised of a rigid material, such as steel. The mandrel shaft 14 defines a mandrel axis 20 and includes a first end portion 21 and a second end portion 22. The first end portion 21 of the mandrel shaft 14 comprises two opposing shaft teeth 24 and 26 extending from the end of the shaft 14 perpendicular to the mandrel axis 20. The shaft teeth 24 and 26 are generally arc or fan shaped when viewed individually. When viewed together, the shaft teeth 24 and 26 form a bow tie shape, as is seen in FIG. 3. (See also FIG. 7.)

Elongated grooves 28 are formed on opposite sides of the first end portion 21 of the mandrel shaft 14. The opposing elongated grooves 28 are parallel to the mandrel axis 20. A circular groove 29 extends circumferentially about the mandrel axis 20 and intersects the elongated grooves 28. The second end portion 22 of the mandrel shaft 14 is generally cylindrical in shape and is configured to be received within a chuck of a rotary tool.

With continued reference to the embodiment shown in FIGS. 1–3, the collar 16 is also comprised of a rigid material such as steel. The collar 16 is cylindrical in shape and forms a sleeve that surrounds a portion of the mandrel shaft 14. The collar 16 includes a head portion 30 with a skirt 32 depending from the head portion 30. As best seen in the embodiment shown in FIG. 9, the head portion 30 includes a circular head wall 31 positioned perpendicular to the skirt 32. An opening 34 is provided through the head portion 30, including the circular wall 31. The collar of FIGS. 5–6 and 8–9 is similar to the collar of FIGS. 1–3, with a few exceptions, as discussed in further detail below. However, in both embodiments, the opening 34 is designed and dimensioned to receive the mandrel shaft 14.

As shown in the embodiments of FIGS. 1–3 and FIGS. 5, 6, 8, 9, two opposing collar teeth 36 and 38 extend from the head 30 about the opening 34, but do not block the opening 34. The collar teeth 36 and 38 are each individually arc or fan shaped and together form two flared portions of a bow tie shape. The collar teeth 36 and 38 include tangs 40 and 41. Each tang 40 or 41 extends toward the opposing collar tooth 38 or 36. The tangs 40 and 41 are configured to be received within the elongated grooves 28 of the mandrel shaft 14.

Figure 9:
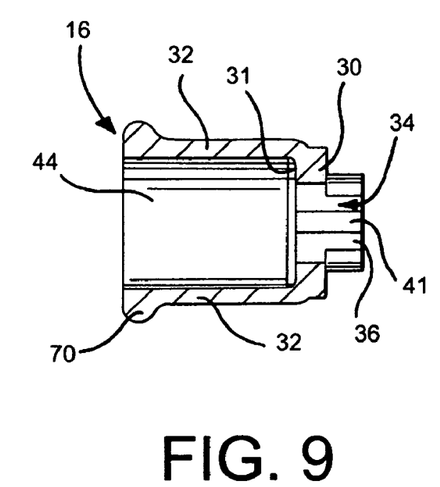
FIG. 9 shows a cross-sectional view of the collar along line A—A of FIG. 8.
Figure 10:
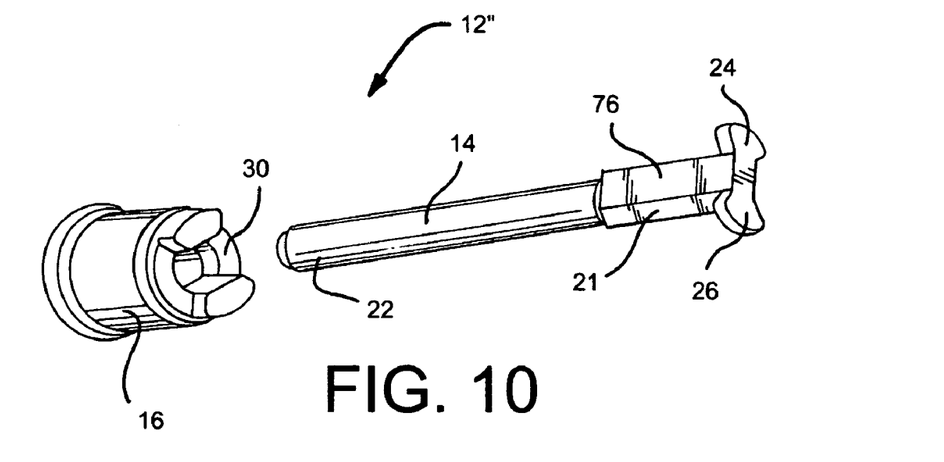
FIG. 10 shows another alternative embodiment of a mandrel assembly for use with a rotary tool with various components of the mandrel assembly omitted for ease of understanding.
Figure 11:
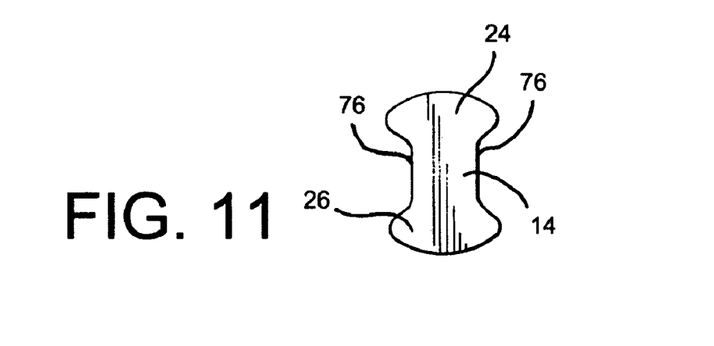
FIG. 11 shows a top elevational view of the shaft of the mandrel assembly of FIG. 10.

As best seen in FIG. 9, the opening 34 in the collar 16 feeds into a cylindrical area 44 defined by the skirt 34 of the collar. This cylindrical area 44 has a diameter greater than that of the mandrel shaft 14, and is dimensioned to receive a spring 46 (see FIG. 5) positioned around the mandrel shaft 14.

As shown in FIG. 3, a retainer or pressure washer 48 is provided to seat in the circular groove 29 of the shaft 14. The spring 46 is retained upon the shaft 14 between the retainer 48 and the circular wall 31 of the collar. As the collar 16 slides along the mandrel shaft 14, the spring biases the collar 16 away from the second end portion 22 of the shaft 14. The retainer 48 provides a stop for the collar 16, allowing the collar 16 to slide along the mandrel shaft 22 between a first position in which the shaft teeth 24 and 26 abut the head 30 of the collar 16 and a second position in which the spring 46 is compressed with the head 30 of the collar 16 forced toward the retainer 48.

With the tangs 40 and 41 of the collar teeth 36 and 38 properly positioned in the elongated grooves 28 of the shaft 14, the collar teeth 36 and 38 are offset from the shaft teeth 24 and 26. This offset allows the collar teeth 36 and 38 to mesh with the shaft teeth 24 and 26, such that the collar teeth may be moved into the same plane that contains the shaft teeth without abutment of the collar teeth and shaft teeth. This meshing action allows the collar teeth 36 and 38 to move freely in the axial direction of the shaft 14 without abutting the shaft teeth 24 and 26. Advantageously, the tangs 40 and 41 slide along the elongated grooves 28 on the mandrel shaft 14 during movement of the collar 16 in the axial direction, and thereby prevent rotation of the collar 16 with respect to the shaft 14 which would disturb the offset relationship between the collar teeth 36 and 38 and the shaft teeth 24 and 26.

An accessory 18 is configured to be attached to the mandrel assembly 12. As shown in FIG. 3, the accessory 18 is configured as a cut-off wheel 19 in one embodiment. The cut-off wheel 19 includes a disc portion 50 having an outer perimeter 52 and a central hub 54. A slot 56 is formed in the central hub 54. The slot defines a first passage 58 and an opposing second passage 59. The first passage 58 and the second passage 59 together form a bow tie shape. A support insert 60 is provided as part of the central hub 54. The support insert 60 is comprised of a strong rigid metallic material. The outer perimeter of the support insert 60 is generally ring shaped. The inner perimeter of the support insert matches the particular shape of the slot 56 of the cut-off wheel 19. In one embodiment, the support insert 60 includes an inner lip that extends into the slot 56 of the central hub 54 and provides an interior support wall for the slot 56. The cut-off wheel 19 is formed by molding the disc portion 50 from a combination of materials that include abrasive materials, resin materials, and one or more fiberglass mesh segments. Such molding process is well-known in the art of manufacturing cut-off wheels. However, typical cut-off wheels do not include support inserts such as support insert 60. Preferably, the support insert 60 is attached to the disc portion 50 by insert molding techniques. Alternatively, the support insert 60 may be secured to the disc portion 50 in any one of a number of different manners such as with adhesives or fasteners, or by friction fitting the support insert 60 within a corresponding opening defined in the disc portion 50.

Figure 4A:
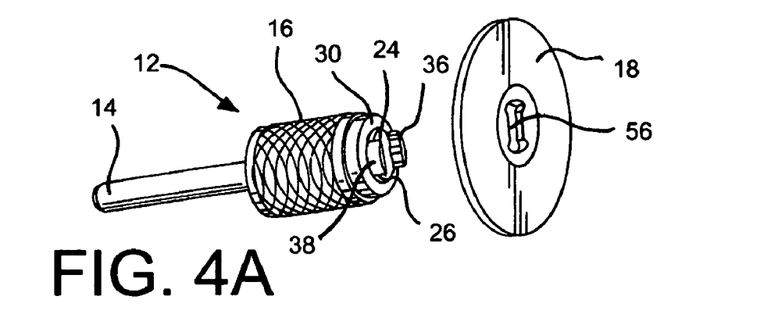
FIGS. 4A–4D show perspective views of the mandrel assembly and accessory of FIG. 1 depicting a series of steps for mounting an accessory to the mandrel assembly.

With reference now to FIGS. 4A–4D, the manner of attaching the accessory 18, such as cut-off wheel 19, to the mandrel assembly 12 is now described. In FIG. 4A, the collar 16 is in the first position with the shaft teeth 24 and 26 of the mandrel shaft 14 abutting the head 30 of the collar 16. In this position, the collar teeth 36 and 38 extend slightly past and mesh with the shaft teeth 24 and 26.

Figure 4B:
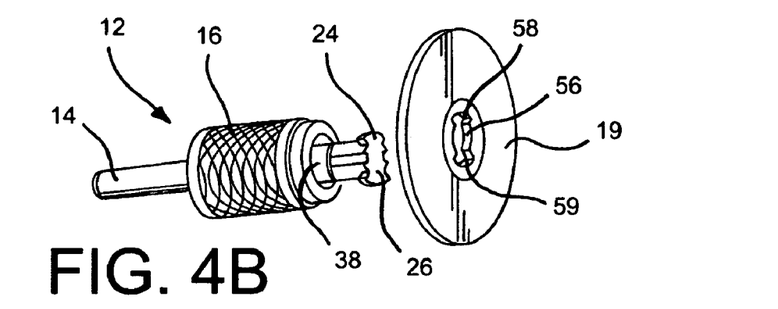

In FIG. 4B, the collar 16 is shown retracted to the second position, with the spring compressed and the shaft teeth 24 and 26 moved forward of the collar teeth 36 and 38. With the collar 16 in this second position, the slot 56 of the cut-off disc 19 is aligned with the shaft 14 such that the first shaft tooth 24 may be passed through the first passage 58 of the slot and the second shaft tooth 26 may be passed thorough the second passage 59 of the slot. The cut-off wheel 19 is then inserted over the shaft teeth 24 and 26 and onto the first end portion 21 of the shaft 14. In this position, the shaft 14 is threaded through the slot 56 of the cut-off wheel.

Figure 4C:
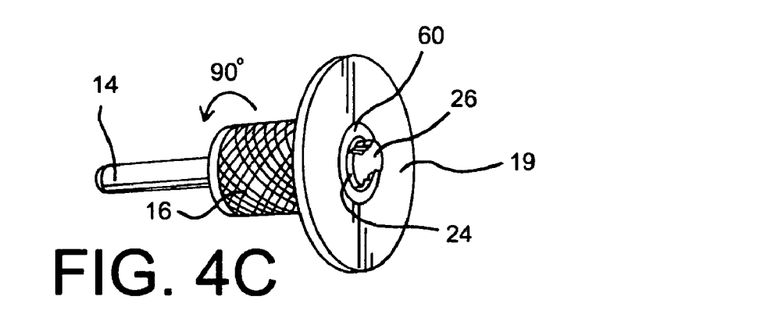
Figure 4D:
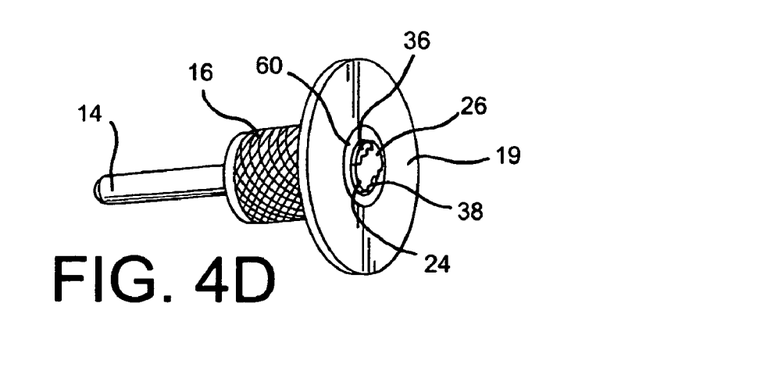

Next, with reference to FIG. 4C, the shaft 14 and collar 16 are rotated 90° relative to the cut-off disc, as noted by the arrow in FIG. 4C. With the cut-off disc in this position, the first collar tooth 36 is aligned with the first passage 58 of the slot 56 and the second collar tooth 38 is aligned with the second passage 59 of the slot. Then, as shown in FIG. 4D, the collar teeth 36 and 38 are moved through the passages 58 and 59 of the cut-off wheel slot 56, causing the collar teeth 36 and 38 to mesh with the shaft teeth 24 and 26. With the mandrel shaft 14 and collar 16 in this position, the spring 46 forces the collar 16 against the cut-off wheel 19, clamping the cut-off wheel 19 between the head 30 of the collar 16 and the shaft teeth 24 and 26. At the same time, the cut-off wheel 19 is prevented from rotating relative to the mandrel assembly 12, because the collar teeth 36 and 38 remain in the slot 56 of the cut-off wheel 19. Likewise, the collar 16 is prevented from rotating relative to the mandrel shaft 14 because the tangs 40 and 41 of the collar teeth 36 and 38 remain in the elongated grooves 28 of the mandrel shaft 14. Alternatively, instead of rotating the shaft 14 and collar 16 by 90° relative to the cut-off disc as noted by the arrow in FIG. 4C, the cut-off disc may be rotated 90° relative to the shaft 14 and the collar 16 while the shaft and collar remains stationary in order to accomplish the same relative movement between the two components.

As described above, a mandrel assembly 12 is disclosed that allows an accessory 18 to be quickly and conveniently coupled to the mandrel assembly 12 without the need for an additional tool such as a screw driver. Likewise, by reversing the above-described actions, the accessory 18 may be quickly and conveniently decoupled from the mandrel assembly 12. Therefore, a mandrel assembly is provided that may be conveniently used with numerous interchangeable accessories such as cut-off wheels, polishing wheels, grinding wheels, sanding discs, or similar articles of manufacture.

Figure 5:
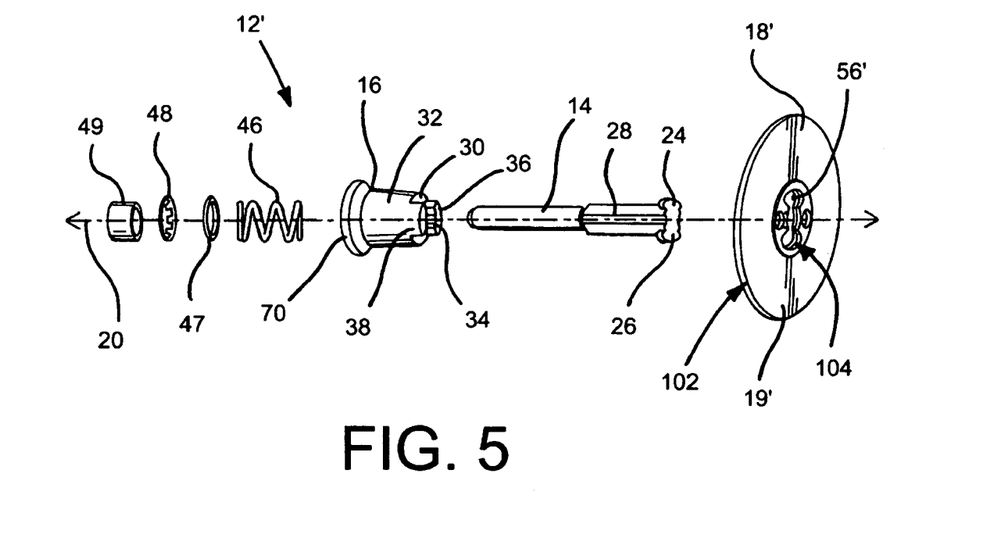
FIG. 5 shows an alternative embodiment of a mandrel assembly and an alternative accessory for use with a rotary tool.
Figure 6:
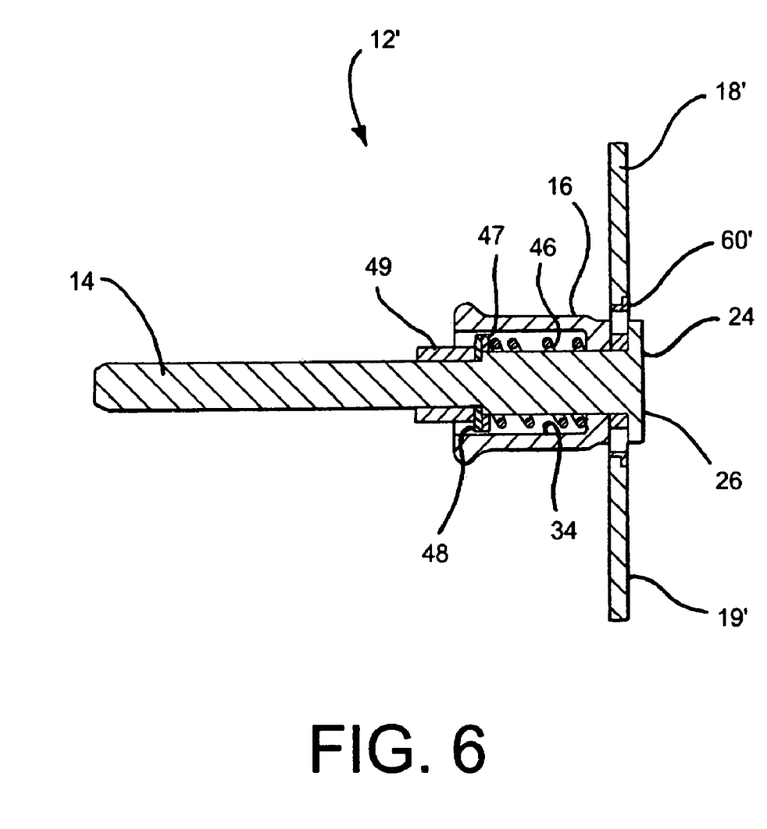
FIG. 6 shows a cross-sectional view of the mandrel assembly and accessory of FIG. 5 when the mandrel assembly is assembled and attached to an accessory.

As alluded to above, FIGS. 5–9 provide an example of an alternative embodiment of a mandrel assembly 12' that incorporates the features of the present invention therein. The mandrel assembly of this embodiment is similar to the mandrel assembly of FIGS. 1–3, but the collar 16 includes an enlarged rim 70 around the base of the skirt 32. (See FIGS. 5, 6, 9.) The enlarged rim 70 provides a gripping surface that is useful to assist a user in urging the collar 16 from the first position where the spring is less compressed (e.g., FIG. 4A) to a second position where the spring is relatively more compressed (e.g., FIG. 4B). Moreover, a ring 47 is positioned around the shaft 14 and interposed between the spring 46 and the retainer 48 as shown in FIGS. 5 and 6. In addition, a sleeve or spacer 49 is positioned around the shaft 14 and located adjacent to the retainer 46 as also shown in FIGS. 5 and 6. An accessory 18' in the form of an alternative cut-off wheel 19' (see also FIGS. 14–17) is configured to be releasably attached to the mandrel assembly 12' as shown in FIGS. 5 and 6.

The sleeve 49 functions to limit depth of insertion of the mandrel assembly 12' into a chuck of a rotary tool (not shown). In particular, when a user inserts the smaller diameter end portion of the shaft 14 into the chuck, physical interaction between the chuck and the sleeve 49 occurs thereby preventing the user from further advancing the mandrel assembly 12' into the chuck. This feature ensures that sufficient space is provided between the chuck and the open end of the collar 16 when the mandrel assembly 12' is clamped to the chuck. Leaving sufficient space between these two components ensures that the collar 16 has enough space for travel in the direction of the mandrel axis 20 (see FIG. 5) so as to allow attachment and removal of the accessory 18' to and from the mandrel assembly 12'.

Figures 12, 13:
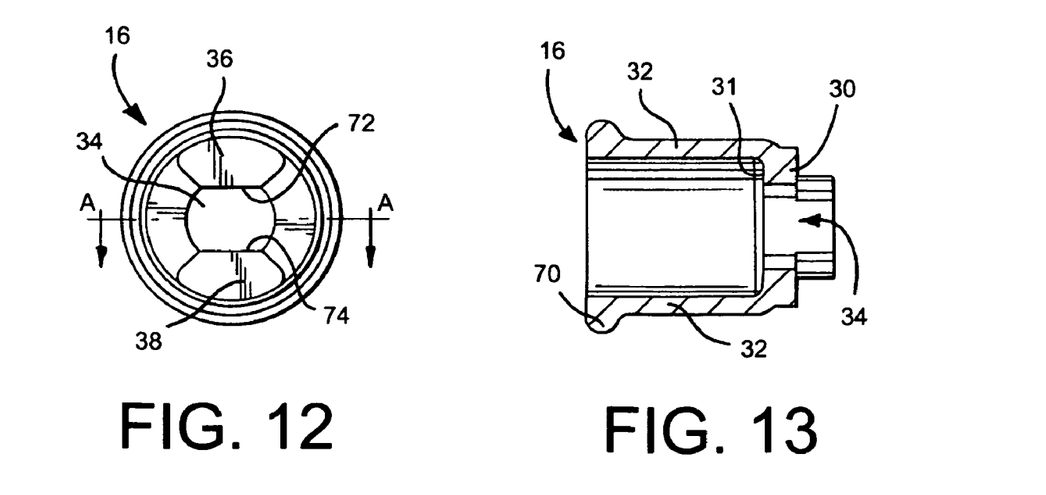
FIG. 12 shows a front elevational view of a collar of the mandrel assembly of FIG. 10.
FIG. 13 shows a cross-sectional view of the collar along line A—A of FIG. 12.

FIGS. 10–13 provide an example of yet another alternative embodiment of a mandrel assembly 12" that incorporates the features of the present invention therein. As shown in FIGS. 10–13, the mandrel assembly 12" of this embodiment is similar to the mandrel assembly 12' of FIGS. 5–9, but the mandrel shaft 14 includes an elongated planar surface 76 on the first end portion of the shaft instead of an elongated groove. This elongated planar surface 76 cooperates with flat portions 72 and 74 on the collar teeth 36 and 38 as shown in FIG. 12 in order to prevent rotation of the collar 16 relative to the shaft 14. Note that the mandrel assembly 12" also includes the spring 46, the ring 47, the retainer 48, and the sleeve 49 which are positioned configured, positioned, and utilized in the same manner shown in FIGS. 5 and 6. However, for ease of understanding and clarity of description, these components have been omitted from FIG. 10. The mandrel assembly 12" is configured to be releasably attached to an accessory (not shown) that is somewhat similar to accessories 18 and 18'. One exception to such an accessory would be that the slot (somewhat similar to slot 56 of FIG. 3 and slot 56' of FIG. 10) need not have exactly the same features as slots 56, 56'. Rather, such a slot would possess a complementary configuration to the shape of the end of the shaft 14 shown in FIG. 11. However, it should be appreciated that accessories 18 and 18' would be capable of being attached to the mandrel assembly 12" even though their slots (e.g. slot 56 of FIG. 3 and slot 56' of FIG. 10) are not exactly complementary to the shape of the end of the shaft 14 shown in FIG. 11.

It should be appreciated that the mandrel assemblies 12, 12', and 12" are somewhat similar in design and thus the same reference numbers have been used to describe similar components of the assemblies for ease of understanding and clarity of description.

Figure 14:
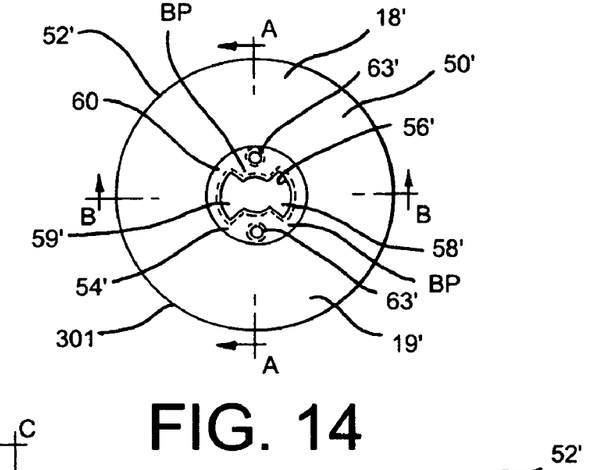
FIG. 14 is an elevational view of the accessory of FIG. 5.
Figure 15:
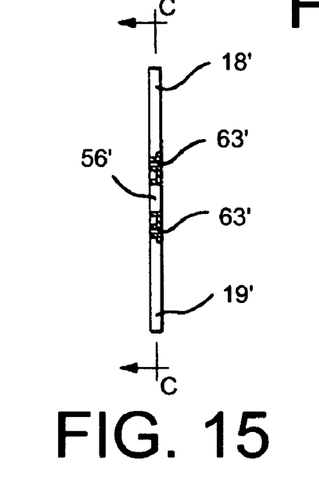
FIG. 15 shows a cross-sectional view of the accessory along line A—A of FIG. 14.
Figure 16:
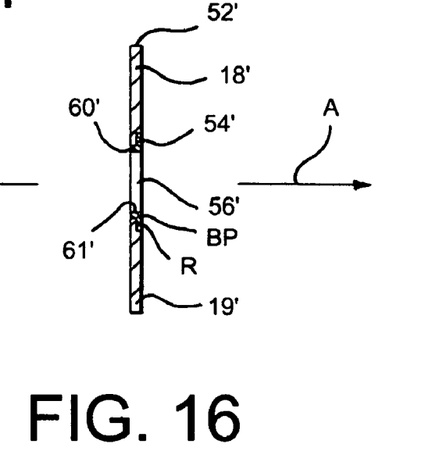
FIG. 16 shows a cross-sectional view of the accessory along line B—B of FIG. 14.
Figure 17:
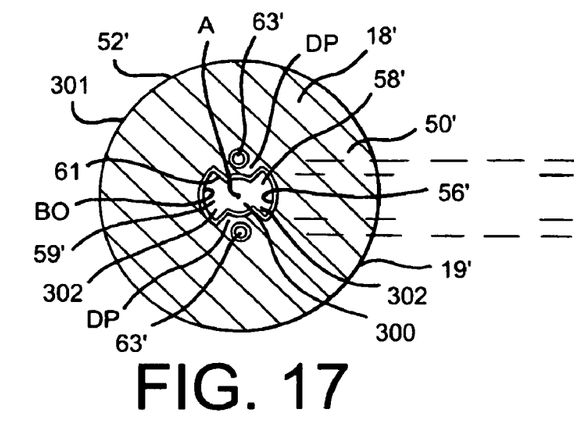
FIG. 17 shows a cross-sectional view of the accessory along line C—C of FIG. 15.

Turning now to FIGS. 14–18, the cut-off wheel 19' is described in more detail. The accessory 18' is made from the same materials and in the same manner as that described hereinabove with regard to the accessory 18. The cut-off wheel 19' includes a disc portion 50' having an outer perimeter 52' and a central hub 54'. A slot 56' is formed in the central hub 54'. The slot defines a first passage 58' and an opposing second passage 59'. The first passage 58' and the second passage 59' together form a bow tie shape. A support insert 60' is provided as part of the central hub 54'. The support insert 60' is comprised of a strong rigid metallic material, and is secured to the disc portion 50' of the cut-off wheel 19'. The outer perimeter of the support insert 60' is generally ring shaped. The inner perimeter of the support insert matches the particular shape of the slot 56' of the cut-off wheel 19'. The support insert 60' includes an inner lip 61' that extends into the slot 56' of the central hub 54' and provides an interior support wall for the slot 56'. The support insert 60' further includes two downwardly extending cylinder portions 63' as shown in FIGS. 14, 15, and 17. Alternatively, FIGS. 18A, 18B 18C, 18D and 18E show another support insert 60" that has identical construction and function as the support insert 60' with a couple of exceptions. The first exception is that the support insert 60" includes a number of anti-rotation spikes 300 that extend downwardly from a bottom surface 301 of the support insert 60" as shown in FIGS. 18A, 18B 18C, 18D and 18E. The spikes 300 function to further inhibit relative rotation of the support insert 60" in relation to the disc portion 50'. The second exception is that instead of having two cylinder portions 63' that extend downwardly as shown in FIGS. 14, 15, and 17, the support insert 60" includes two circular openings 63" as shown in FIGS. 18A, 18B 18C, 18D and 18E. The two circular openings 63" are created by a lancing or drilling operation that includes advancing a tool bit into a top surface of the support insert 60" and out through a bottom surface of the support insert 60". Such an operation causes a certain amount of displaced material to extend downwardly from the bottom surface 301 around the periphery of each circular opening 63". This certain amount of displaced material functions, as the anti-rotation spikes 300 do, to further inhibit relative rotation of the support insert 60" in relation to the disc portion 50'.

Figure 18:
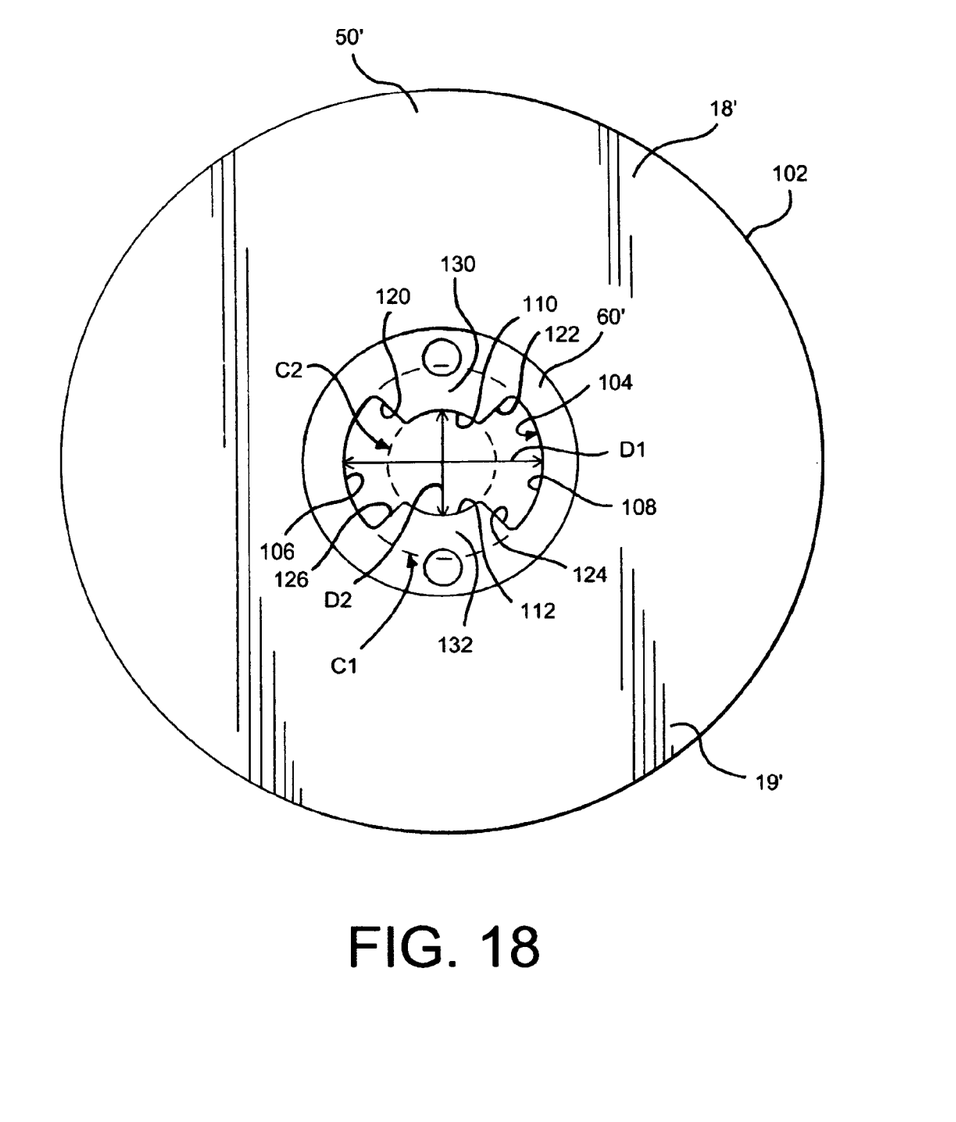
FIG. 18 shows an enlarged front elevational view of the accessory shown in FIG. 5.
Figure 18A:
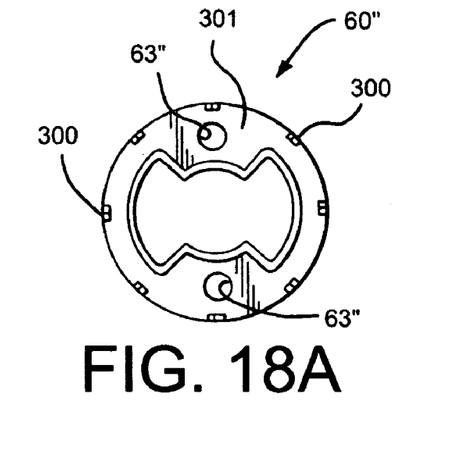
FIGS. 18A, 18B, 18C, 18D, and 18E show various views of an alternative embodiment of a support insert that may be used in place of the support insert of the accessory shown in FIGS. 14–18.
Figure 18B:
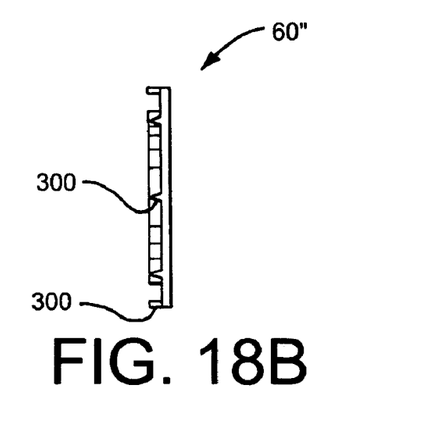
Figure 18C:
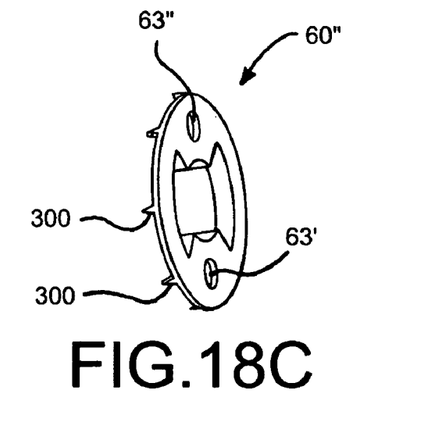
Figure 18D:
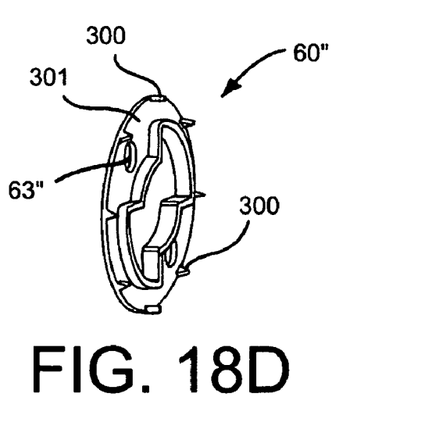
Figure 18E:
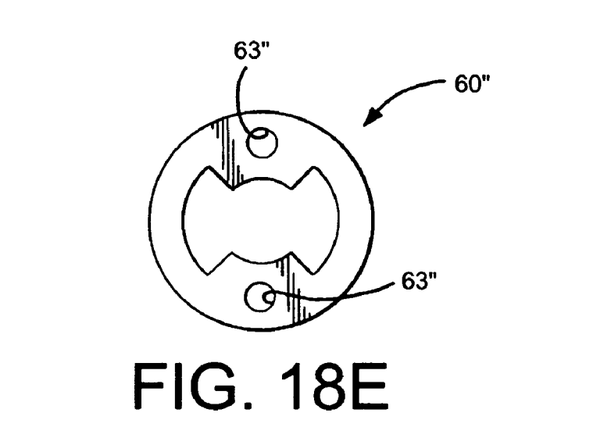

As shown in FIG. 18, the accessory 18' includes an outer wall structure 102 that defines a circular outer periphery. The accessory 18' further includes an inner wall structure 104 that defines a coupling opening. The inner wall structure 104 includes a first inner wall portion 106, a second inner wall portion 108, a third inner wall portion 110, and a fourth inner wall portion 112. The first inner wall portion 106 defines an arc of a first circle C1 having a first diameter D1. The second inner wall portion 108 defines another arc of the first circle C1 having the first diameter D1. The third inner wall portion 110 defines an arc of a second circle C2 having a second diameter D2. The fourth inner wall portion 112 defines another arc of the second circle C2 having the second diameter D2. The first diameter D1 is greater than the second diameter D2. Each of the first arc and the second arc extends for a distance that is greater than forty-five (45) degrees in relation to the first circle C1. Preferably, each of the first arc and the second arc extends for a distance that is approximately equal to ninety (90) degrees in relation to the first circle C1.

The inner wall structure 104 further includes (i) a planar fifth inner wall portion 120 connecting the first inner wall portion 106 to the third inner wall portion 110, (ii) a planar sixth inner wall portion 122 connecting the third inner wall portion 110 to the second inner wall portion 108, (iii) a planar seventh inner wall portion 124 connecting the second inner wall portion 108 to the fourth inner wall portion 112, and (iv) a planar eighth inner wall portion 126 connecting the first inner wall portion 106 to the fourth inner wall portion 112.

The accessory 18' further includes a first clamping flange 130 that is offset from the first inner wall portion 106 and the second inner wall portion 108. The first clamping flange 130 includes the third inner wall portion 110 as shown in FIG. 18. Also, the accessory 18' additionally includes a second clamping flange 132 that is offset from the first inner wall portion 106 and the second inner wall portion 108. The second clamping flange 132 includes the fourth inner wall portion 112 as also shown in FIG. 18.

Figure 19:
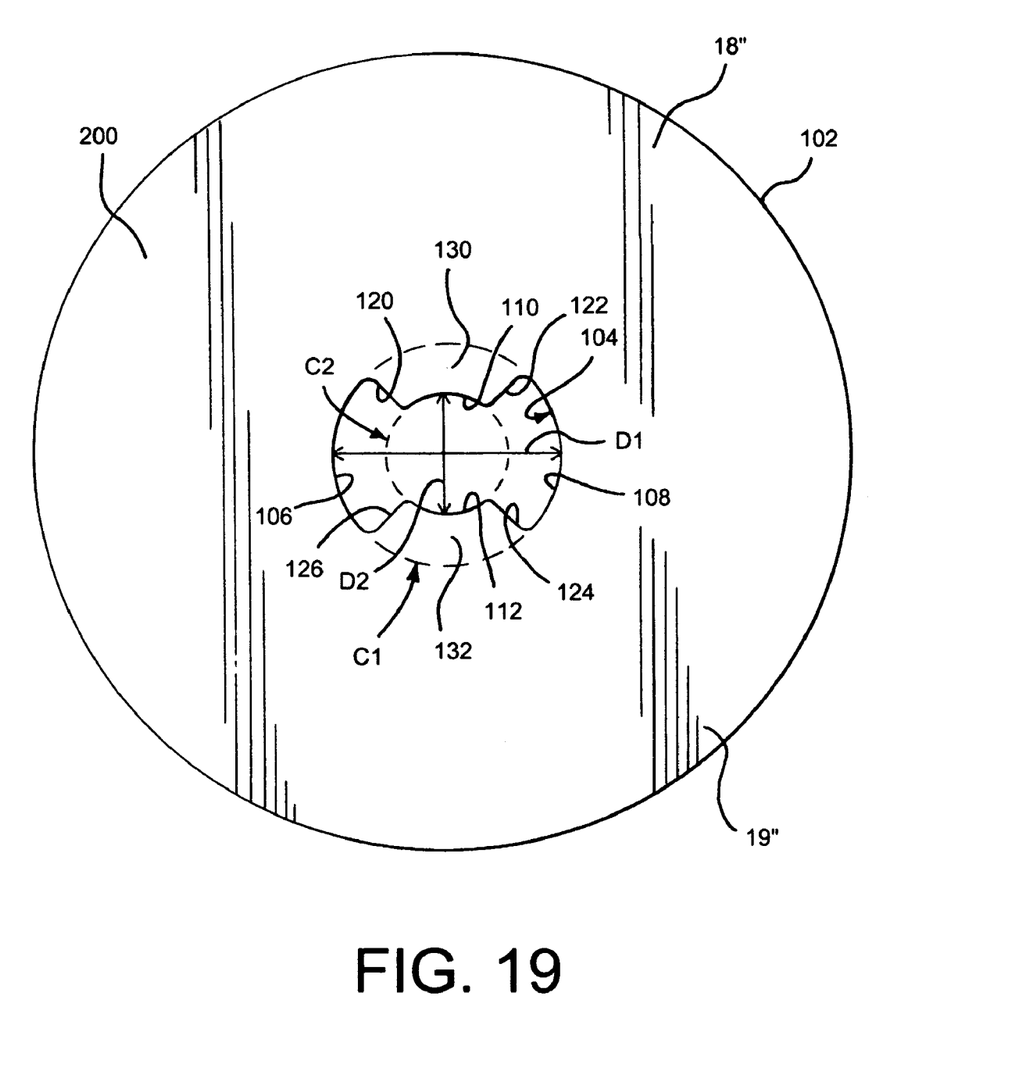
FIG. 19 shows another embodiment of an accessory that may be used with the mandrel assemblies of FIGS. 1, 5, and 10.

FIG. 19 shows another alternative embodiment of an accessory 18" that may be used with any of the mandrel assemblies 12, 12', and 12" described herein, and in the same manner described herein as the accessory 18' is described herein as being used with any of mandrel assemblies 12, 12', and 12". Since the accessory 18" is somewhat similar in design to the accessory 18' described above, the same reference numbers have been used to describe similar components of the assemblies for ease of understanding and clarity of description. The difference between the accessory 18' and the accessory 18" is that the accessory 18" does not include an insert. Rather, the accessory 18" includes a body 200 that includes the outer wall structure 102 and the inner wall structure 104. The body 200 is made from the same materials and in the same manner as that described hereinabove with regard to the disc portion 50 of the accessory 18.

Figure 20:
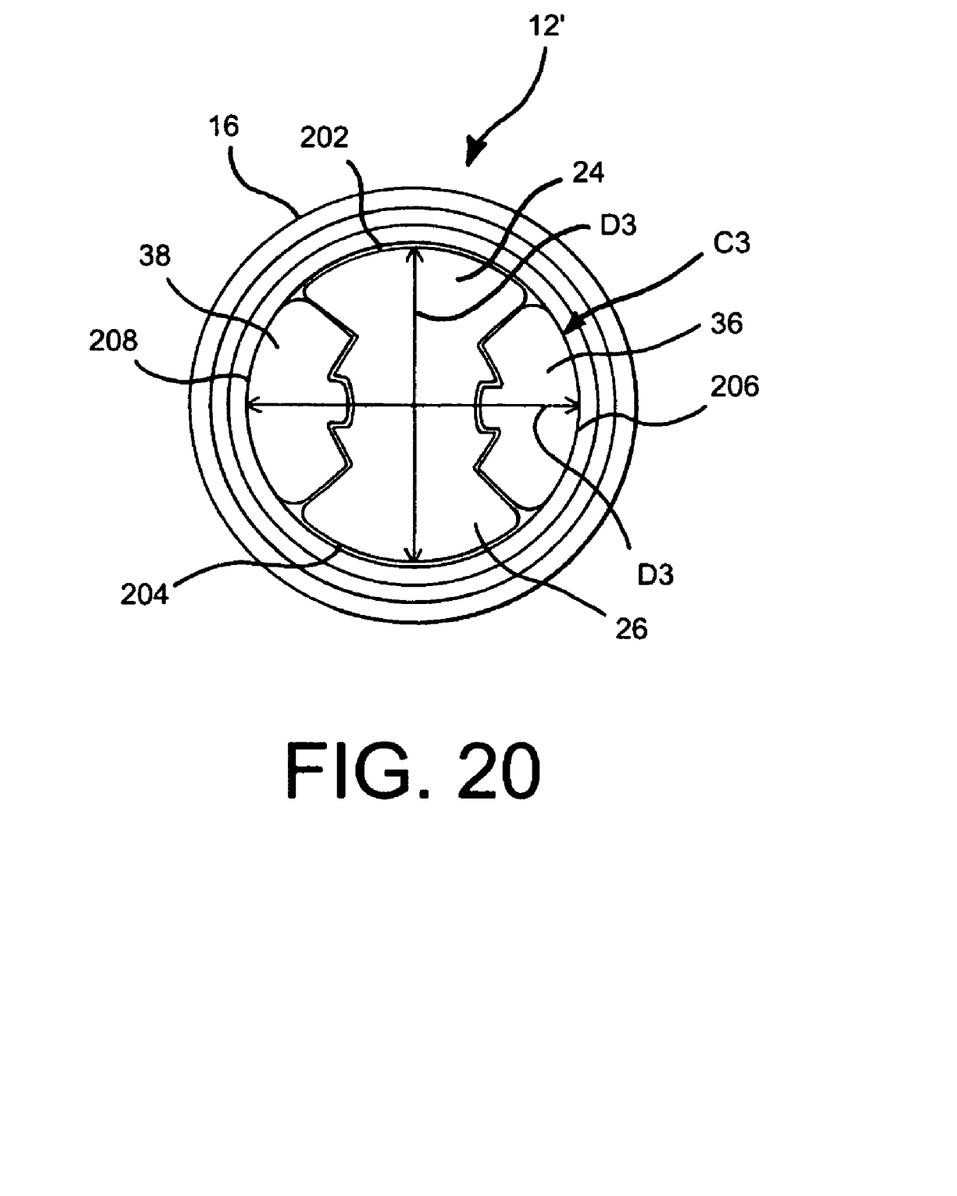
FIG. 20 shows a front elevational view of the mandrel assembly of FIG. 5 in an assembled state.

Turning now to FIG. 20, there is shown a front elevational view of the mandrel assembly 12' in an assembled state. The first shaft tooth 24 includes a first outer shaft tooth wall portion 202 defining an arc of a third circle C3 having a third diameter D3. The second shaft tooth 26 includes a second outer shaft tooth wall portion 204 defining an arc of the third circle C3 having the third diameter D3. The first collar tooth 36 includes a first outer collar tooth wall portion 206 defining an arc of the third circle C3 having the third diameter D3. And the second collar tooth 38 includes a second outer collar tooth wall portion 208 defining an arc of the third circle C3 having the third diameter D3. It should be appreciated that the third diameter D3 is greater than the second diameter D2 (see FIGS. 18 and 19), but less than the first diameter D1 (see FIGS. 18 and 19). The allows the accessory 18, 18' and 18" to be secured to and firmly held by the mandrel assembly 12, 12', and 12". Also, each of the arcs defined by the first outer shaft tooth wall portion 202, the second outer shaft tooth wall portion 204, the first outer collar tooth wall portion 206, and the second outer collar tooth wall portion 208 extends for a distance that is greater than forty-five (45) degrees in relation to the third circle C3. Preferably, each of the arcs defined by the first outer shaft tooth wall portion 202, the second outer shaft tooth wall portion 204, the first outer collar tooth wall portion 206, and the second outer collar tooth wall portion 208 extends for a distance that is approximately equal to ninety (90) degrees in relation to the third circle C3.

Figure 17A:
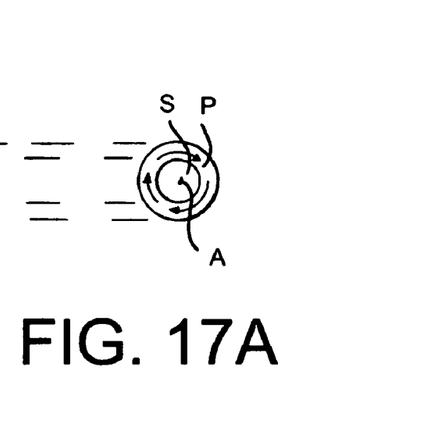
FIG. 17A depicts (i) the space S that contains the first opening portion 300 during rotation of the body of the accessory of FIG. 17 about the axis A, and (ii) the path P that both the drive portions DP and the second opening portions 302 travel during rotation of the body of the accessory of FIG. 17 about the axis A.

As can be seen in FIGS. 14–18, the accessory 18' includes a body that defines an axis of rotation A and has a work piece contacting surface 301 and two drive portions DP. The body has defined therein a body opening BO including a first opening portion 300 and two second opening portions 302. The accessory 18' further includes the support insert 60' located within the body opening BO. The first opening portion 300 is contained within a space S depicted in FIG. 17A during rotation of the body about the axis A. Both the drive portions DP and the second opening portions 302 are advanced through a path P depicted in FIG. 17A during rotation of the body about the axis A. As depicted in FIG. 17A, the path is located outside of the space S. Note that the body of the accessory 18' defines a recess R that surrounds the body opening BO, and a base portion BP of the support insert 60' extends from the inner lip 61' of the support insert 60'.

Although the present invention has been described with respect to certain preferred embodiments, it will be appreciated by those of skill in the art that other implementations and adaptations are possible. For example, differently shaped teeth may be provided on the shaft and the collar which are different from the teeth described herein. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A mandrel and accessory combination, comprising:
    (a) a mandrel assembly including:
        a shaft component defining an axis and having (i) a first portion configured to be received in a chuck of a power tool, and (ii) a second portion having a first shaft tooth and a second shaft tooth each extending in a perpendicular manner with respect to said axis; and
        a collar component defining a passage through which said shaft component extends, said collar component having a first collar tooth and a second collar tooth, and
    (b) an accessory including:
        an outer wall structure defining a circular outer periphery;
        an inner wall structure defining a coupling opening,
        wherein said inner wall structure includes (i) a first inner wall portion defining a first arc of a first circle having a first diameter, (ii) a second inner wall portion defining a second arc of said first circle having said first diameter, (iii) a third inner wall portion defining a third arc of a second circle having a second diameter, and (iv) a fourth inner wall portion defining a fourth arc of said second circle having said second diameter,
        wherein said first shaft tooth includes a first outer shaft tooth wall portion defining a fifth arc of a third circle having a third diameter,
        wherein said second shaft tooth includes a second outer shaft tooth wall portion defining a sixth arc of said third circle having said third diameter,
        wherein said first collar tooth includes a first outer collar tooth wall portion defining a seventh arc of said third circle having said third diameter,
        wherein said second collar tooth includes a second outer collar tooth wall portion defining an eighth arc of said third circle having said third diameter,
        wherein said first diameter is greater than said second diameter,
        wherein said first diameter is greater than said third diameter, and
        wherein said second diameter is less than said third diameter.

2. The mandrel and accessory combination of claim 1, wherein said collar component is movable in relation to said shaft component between (i) a first relative position in which said first collar tooth and said second collar tooth are positioned in mating relationship with said first shaft tooth and said second shaft tooth, and (ii) a second relative position in which said first collar tooth and said second collar tooth are positioned out of mating relationship with said first shaft tooth and said second shaft tooth.

3. The mandrel and accessory combination of claim 2, further comprising a spring configured to urge said collar component toward said first relative position.

4. The mandrel and accessory combination of claim 2, wherein:
    said shaft component defines at least one elongated groove extending in a parallel manner with respect to said axis,
    at least one of said first collar tooth and said second collar tooth includes a tang positioned in said at least one elongated groove, and
    said tang rides in said at least one elongated groove during movement of said collar component between said first relative position and said second relative position.

5. The mandrel and accessory combination of claim 3, further comprising a retainer attached to said shaft component and configured to retain said spring within said passage of said collar component.

6. The mandrel and accessory combination of claim 1, wherein:
    each of said first arc and said second arc extends for a first distance that is greater than forty-five (45) degrees in relation to said first circle, and
    each of said third arc and said fourth arc extends for a second distance that is greater than forty-five (45) degrees in relation to said second circle.

7. The mandrel and accessory combination of claim 1 wherein:
    each of said first arc and said second arc extends for a first distance that is approximately equal to ninety (90) degrees in relation to said first circle, and
    each of said third arc and said fourth arc extends for a second distance that is approximately equal to ninety (90) degrees in relation to said second circle.

8. The mandrel and accessory combination of claim 1, wherein said accessory further comprises:
    a body that includes said outer wall structure; and
    an insert that includes said inner wall structure.

9. The mandrel and accessory combination of claim 8, wherein:
    said body includes a fiberglass mesh material, and
    said insert is made of a metallic material.

10. The mandrel and accessory combination of claim 8, wherein said insert includes:
    a base portion having (i) an outer portion defining a circumferential outer edge, and (ii) an inner portion, and
    a lip portion extending from said inner portion of said base portion.

11. The mandrel and accessory combination of claim 10, wherein said inner wall structure includes said lip portion.

12. The mandrel and accessory combination of claim 1, wherein said accessory further includes:
    a first clamping flange offset from said first inner wall portion and said second inner wall portion, said first clamping flange including said third inner wall portion; and
    a second clamping flange offset from said first inner wall portion and said second inner wall portion, said second clamping flange including said fourth inner wall portion.

13. The mandrel and accessory combination of claim 12, wherein said accessory further comprises:
    a body that includes said outer wall structure; and
    an insert that includes said inner wall structure, wherein said first clamping flange includes a first part of said insert and a first part of said body, and wherein said second clamping flange includes a second part of said insert and a second part of said body.

14. The mandrel and accessory combination of claim 1, wherein said accessory further comprises a body that includes (i) said outer wall structure; and (ii) said inner wall structure.

15. The mandrel and accessory combination of claim 14, wherein said body includes a fiberglass mesh material.

16. The mandrel and accessory combination of claim 1, wherein:

each of said fifth arc, said sixth arc, said seventh arc, and said eighth arc extends for a distance that is greater than forty-five (45) degrees in relation to said third circle.

17. The mandrel and accessory combination of claim 1 wherein:

each of said fifth arc, said sixth arc, said seventh arc, and said eighth arc extends for a distance that is approximately equal to ninety (90) degrees in relation to said third circle.

18. A mandrel assembly, comprising:

a shaft component defining an axis and having (i) a first portion configured to be received in a chuck of a power tool, and (ii) a second portion having a first shaft tooth and a second shaft tooth each extending in a perpendicular manner with respect to said axis; and a collar component defining a passage through which said shaft component extends, said collar component having a first collar tooth and a second collar tooth, wherein said first shaft tooth includes a first outer tooth wall portion defining a first arc of a circle having a diameter, wherein said second shaft tooth includes a second outer shaft tooth wall portion defining a second arc of said circle having said diameter, wherein said first collar tooth includes a first outer collar tooth wall portion defining a third arc of said circle having said diameter, wherein said second collar tooth includes a second outer collar tooth wall portion defining a fourth arc of said circle having said diameter, and wherein said collar component is movable in relation to said shaft component between (i) a first relative position in which said first collar tooth and said second collar tooth are positioned in mating relationship with said first shaft tooth and said second shaft tooth, and (ii) a second relative position in which said first collar tooth and said second collar tooth are positioned out of mating relationship with said first shaft tooth and said second shaft tooth.

19. A mandrel assembly, comprising:

a shaft component defining an axis and having (i) a first portion configured to be received in a chuck of a power tool, and (ii) a second portion having a first shaft tooth and a second shaft tooth each extending in a perpendicular manner with respect to said axis; and a collar component defining a passage through which said shaft component extends, said collar component having a first collar tooth and a second collar tooth, wherein said first shaft tooth includes a first outer shaft tooth wall portion defining a first arc of a circle having a diameter, wherein said second shaft tooth includes a second outer shaft tooth wall portion defining a second arc of said circle having said diameter, wherein said first collar tooth includes a first outer collar tooth wall portion defining a third arc of said circle having said diameter, wherein said second collar tooth includes a second outer collar tooth wall portion defining a fourth arc of said circle having said diameter, and further comprising a spring configured to urge said collar component toward said first relative position.

20. The mandrel assembly of claim 18, wherein:

said shaft component defines at least one elongated groove extending in a parallel manner with respect to said axis;

at least one of said first collar tooth and said second collar tooth includes a tang positioned in said at least one elongated groove, and said tang rides in said at least one elongated groove during movement of said collar component between said first relative position and said second relative position.

21. The mandrel assembly of claim 19, further comprising a retainer attached to said shaft component for retaining said spring within said passage of said collar component.

22. A rotary tool accessory, comprising:

an outer wall structure defining a circular outer periphery;

an inner wall structure defining a coupling opening, wherein said inner wall structure includes (i) a first inner wall portion, (ii) second inner wall portion, (iii) a third inner wall portion, and (iv) a fourth inner wall portion, wherein said first inner wall portion defines a first arc of a first circle having a first diameter, wherein said second inner wall portion defines a second arc of said first circle having said first diameter, wherein said third inner wall portion defines a third arc of a second circle having a second diameter, wherein said fourth inner wall portion defines a fourth arc of said second circle having said second diameter, and wherein said first diameter is greater than said second diameter.

23. The rotary tool accessory of claim 22, wherein:

each of said first arc and said second arc extends for a first distance that is greater than forty-five (45) degrees in relation to said first circle, and each of said third arc and said fourth arc extends for a second distance that is greater than forty-five (45) degrees in relation to said second circle.

24. The rotary tool accessory of claim 22 wherein:

each of said first arc and said second arc extends for a first distance that is approximately equal to ninety (90) degrees in relation to said first circle, each of said third arc and said fourth arc extends for a second distance that is approximately equal to ninety (90) degrees in relation to said second circle.

25. The rotary tool accessory of claim 22, wherein said inner wall structure further includes:

a planar fifth inner wall portion connecting said first inner wall portion to said third inner wall portion, a planar sixth inner wall portion connecting said third inner wall portion to said second inner wall portion, a planar seventh inner wall portion connecting said second inner wall portion to said fourth inner wall portion, and a planar eighth inner wall portion connecting said first inner wall portion to said fourth inner wall portion.

26. The rotary tool accessory of claim 22, further comprising:

a body that includes said outer wall structure; and an insert that includes said inner wall structure.

27. The rotary tool accessory of claim 26, wherein:

said body includes a fiberglass mesh material, and said insert is made of a metallic material.

28. The rotary tool accessory of claim 26, wherein said insert includes:
a base portion having (i) an outer portion defining a circumferential outer edge, and (ii) an inner portion, and
a lip portion extending from said inner portion of said base portion.

29. The rotary tool accessory of claim 28, wherein said inner wall structure includes said lip portion.

30. The rotary tool accessory of claim 22, further comprising:
a first clamping flange offset from said first inner wall portion and said second inner wall portion, said first clamping flange including said third inner wall portion; and
a second clamping flange offset from said first inner wall portion and said second inner wall portion, said second clamping flange including said fourth inner wall portion.

31. The rotary tool accessory of claim 30, further comprising:
a body that includes said outer wall structure; and
an insert that includes said inner wall structure,
wherein said first clamping flange includes a first part of said insert and a first part of said body, and
wherein said second clamping flange includes a second part of said insert and a second part of said body.

32. The rotary tool accessory of claim 22, further comprising a body that includes (i) said outer wall structure; and (ii) said inner wall structure.

33. The rotary tool accessory of claim 32, wherein said body includes a fiberglass mesh material.

34. A rotary tool accessory, comprising:
a workpiece contacting portion; and
an inner wall structure defining a coupling opening,
wherein said inner wall structure includes (i) a first inner wall portion, and (ii) second inner wall portion,
wherein said first inner wall portion defines a first arc of a first circle having a first diameter,
wherein said second inner wall portion defines a second arc of a second circle having a second diameter,
wherein said first diameter is greater than said second diameter,
further comprising a clamping flange offset from said first inner wall portion, said first clamping flange including said second inner wall portion.

35. The rotary tool accessory of claim 34, wherein:
said first arc extends for a first distance that is greater than forty-five (45) degrees in relation to said first circle, and
said second arc extends for a second distance that is greater than forty-five (45) degrees in relation to said second circle.

36. The rotary tool accessory of claim 34, wherein:
said first arc extends for a first distance that is approximately equal to ninety (90) degrees in relation to said first circle, and
said second extends for a second distance that is approximately equal to ninety (90) degrees in relation to said second circle.

37. A rotary tool accessory, comprising:
a workpiece contacting portion; and
an inner wall structure defining a coupling opening,
wherein said inner wall structure includes (i) a first inner wall portion, and (ii) second inner wall portion,
wherein said first inner wall portion defines a first arc of a first circle having a first diameter,
wherein said second inner wall portion defines a second arc of a second circle having a second diameter,
wherein said first diameter is greater than said second diameter,
further comprising:
a body that includes an outer wall structure; and
an insert that includes said inner wall structure.

38. The rotary tool accessory of claim 37, wherein:
said body includes a fiberglass mesh material, and
said insert is made of a metallic material.

39. The rotary tool accessory of claim 37, wherein said insert includes:
a base portion having (i) an outer portion defining a circumferential outer edge, and (ii) an inner portion, and
a lip portion extending from said inner portion of said base portion,
wherein said inner wall structure includes said lip portion.

* * * * *